US010464753B2

United States Patent
Masciarelli

(10) Patent No.: US 10,464,753 B2
(45) Date of Patent: Nov. 5, 2019

(54) POP-UP WHEEL DEVICE FOR USE IN MATERIAL HANDLING EQUIPMENT

(71) Applicant: OMTEC, CORP., Marlborough, MA (US)

(72) Inventor: Shawn Morris Masciarelli, Marlborough, MA (US)

(73) Assignee: OMTEC, CORP.

( * ) Notice: Subject to any disclaimer, the term of this patent is extended or adjusted under 35 U.S.C. 154(b) by 0 days.

(21) Appl. No.: 15/925,845

(22) Filed: Mar. 20, 2018

(65) Prior Publication Data

US 2019/0084765 A1 Mar. 21, 2019

Related U.S. Application Data

(60) Provisional application No. 62/560,458, filed on Sep. 19, 2017.

(51) Int. Cl.
*B65G 13/12* (2006.01)
*B65G 39/09* (2006.01)
(Continued)

(52) U.S. Cl.
CPC ............. *B65G 13/12* (2013.01); *B65G 39/09* (2013.01); *F15B 15/1433* (2013.01);
(Continued)

(58) Field of Classification Search
CPC .... B65G 13/065; B65G 13/12; B65G 39/025; B65G 2207/34
(Continued)

(56) References Cited

U.S. PATENT DOCUMENTS 3,565,233 A  2/1971  Hinman
3,712,454 A  1/1973  McKee
(Continued)

FOREIGN PATENT DOCUMENTS

GB  2348631 A  10/2000
JP  5043033 A  2/1993
JP  2002187608 A  7/2002

OTHER PUBLICATIONS

Sales literature for PBT Ball Transfer, Omtec Corp., Marlborough, MA (2018).
(Continued)

*Primary Examiner* — James R Bidwell
(74) *Attorney, Agent, or Firm* — Kriegsman & Kriegsman

(57) ABSTRACT

A pop-up wheel device for use in material handling equipment. In one embodiment, the pop-up wheel device includes a housing, which is a can of generally track-shaped transverse cross-section. A nipple is mounted in the housing bottom to permit fluid under pressure to pass to and from the interior of the housing. A cap, which includes a central opening, is positioned over and is secured to the housing. A piston is slidably mounted within the housing between a lower position and an upper position. A seal is fitted around a lower portion of the piston and creates an air-tight chamber between the piston and the housing. A spring biases the piston towards the lower position. A wheel that is freely rotatable in one direction is coupled to the piston using a wheel mount. The wheel may be removed from the wheel mount without removing the cap from the housing.

17 Claims, 14 Drawing Sheets

(51) Int. Cl.
*F15B 15/14* (2006.01)
*F16C 13/00* (2006.01)
*F16C 29/04* (2006.01)

(52) U.S. Cl.
CPC ........ *F15B 15/1447* (2013.01); *F16C 13/006* (2013.01); *F16C 29/04* (2013.01); *F16C 2326/58* (2013.01)

(58) Field of Classification Search
USPC ................ 198/370.1, 371.3, 782; 193/35 SS
See application file for complete search history.

(56) References Cited

U.S. PATENT DOCUMENTS

| | | | |
|---|---|---|---|
| 3,967,718 | A | 7/1976 | Monahan |
| 3,978,975 | A | 9/1976 | Herbes et al. |
| 3,983,988 | A | 10/1976 | Maxted et al. |
| 4,285,550 | A | 8/1981 | Blackburn et al. |
| 4,328,889 | A | 5/1982 | Maxted |
| 4,372,435 | A | 2/1983 | Bradbury |
| 4,589,542 | A | 5/1986 | Steadman |
| 4,598,815 | A | 7/1986 | Adama |
| 4,627,526 | A | 12/1986 | Masciarelli |
| 4,660,994 | A | 4/1987 | Masciarelli |
| 4,697,694 | A | 10/1987 | Huber |
| 4,703,844 | A | 11/1987 | Jahns |
| 4,706,793 | A | 11/1987 | Masciarelli |
| 4,732,490 | A | 3/1988 | Masciarelli |
| 4,746,003 | A | 5/1988 | Yu et al. |
| 4,792,037 | A | 12/1988 | Huber |
| 4,913,277 | A | 4/1990 | Zoergiebel et al. |
| 4,949,837 | A | 8/1990 | Huber |
| 5,029,693 | A | 7/1991 | Williams |
| 5,042,645 | A | 8/1991 | Pritchard |
| 5,076,412 | A | 12/1991 | Huber |
| 5,160,017 | A | 11/1992 | Goodman et al. |
| 5,219,058 | A | 6/1993 | Sundseth |
| 5,222,585 | A | 6/1993 | van der Werff |
| 5,350,048 | A | 9/1994 | Wylie |
| 5,516,211 | A | 5/1996 | Barnes et al. |
| 5,551,543 | A | 9/1996 | Mattingly et al. |
| 5,921,374 | A | 7/1999 | Takino et al. |
| 5,971,133 | A | 10/1999 | Wilkins |
| 6,019,211 | A | 2/2000 | Masciarelli, Jr. |
| 6,120,185 | A | 9/2000 | Masciarelli, Jr. |
| 6,164,429 | A | 12/2000 | Masciarelli, Jr. |
| 6,223,880 | B1 | 5/2001 | Caspi et al. |
| 6,279,716 | B1 | 8/2001 | Kayatani et al. |
| 6,340,083 | B1 | 1/2002 | Zhou et al. |
| 6,401,900 | B1 | 6/2002 | Masciarelli, Jr. |
| 6,457,865 | B1 | 10/2002 | Masciarelli, Jr. |
| 6,516,934 | B2 | 2/2003 | Masciarelli, Jr. |
| 6,619,465 | B1 | 9/2003 | Gebhardt |
| 6,786,318 | B1 | 9/2004 | Pace et al. |
| 6,889,815 | B2 | 5/2005 | Kanamori et al. |
| 6,938,751 | B1 | 9/2005 | Eubanks et al. |
| 6,981,580 | B2 | 1/2006 | Meyer |
| 7,040,478 | B2 | 5/2006 | Ehlert |
| 7,073,651 | B2 | 7/2006 | Costanzo et al. |
| 7,178,659 | B2 | 2/2007 | Evans et al. |
| 7,431,148 | B2 | 10/2008 | Li et al. |
| 7,581,632 | B2 | 9/2009 | Wallace et al. |
| 7,673,738 | B2 * | 3/2010 | McConnell ............... B60P 1/52 198/782 |
| 8,011,307 | B2 | 9/2011 | Marcelli |
| 8,016,099 | B2 * | 9/2011 | Eck .......................... B64D 9/00 198/782 |
| 8,844,600 | B2 | 9/2014 | Hirata |
| 8,960,401 | B2 * | 2/2015 | Parsons .................. B23K 37/00 193/35 SS |
| 8,978,879 | B2 | 3/2015 | Fourney |
| 2009/0120767 | A1 * | 5/2009 | Stewart .................... B64D 9/00 198/782 |
| 2010/0181168 | A1 * | 7/2010 | Eck .......................... B64D 9/00 198/782 |

OTHER PUBLICATIONS

Sales literature for Insert Wheels, Omtec Corp., Marlborough, MA (2018), together with a photo showing the aforementioned Insert Wheel and a photo showing the end cap for the aforementioned Insert Wheel.

Sales literature for Conveyor Wheels/Skate Wheels, Frantz Manufacturing Co., Sterling, IL (2019).

* cited by examiner

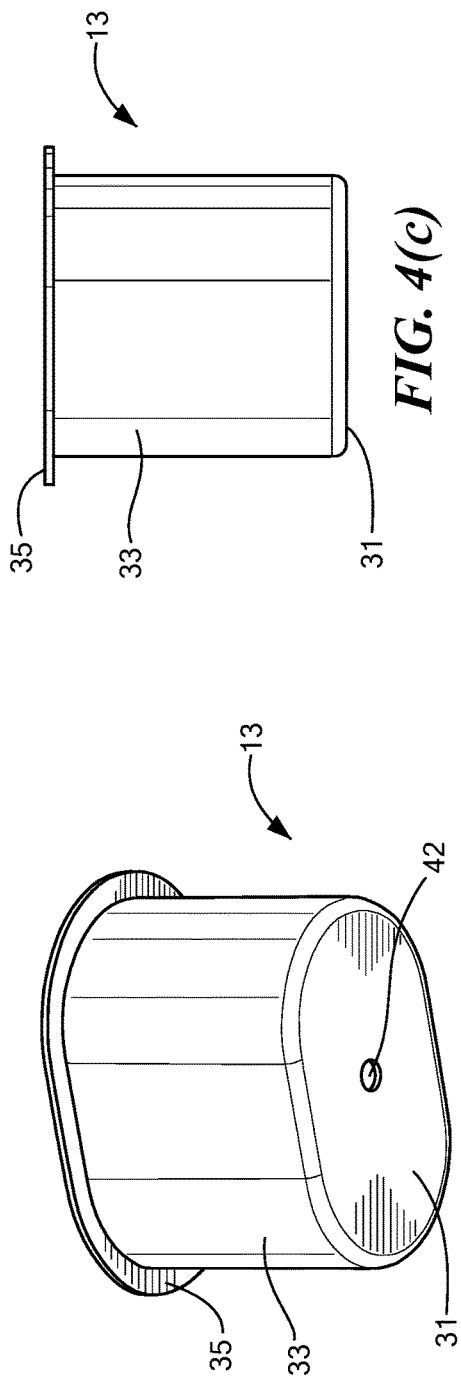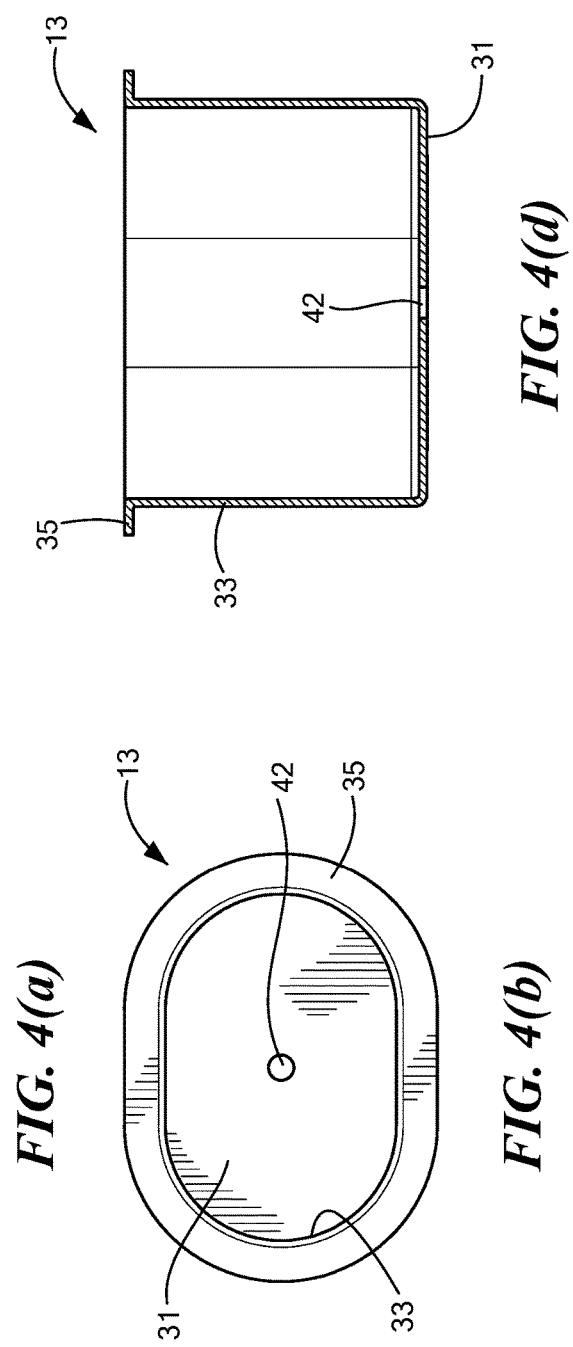
FIG. 4(a)
FIG. 4(b)
FIG. 4(c)
FIG. 4(d)

POP-UP WHEEL DEVICE FOR USE IN MATERIAL HANDLING EQUIPMENT

BACKGROUND OF THE INVENTION

The present invention relates generally to material handling equipment and relates more particularly to pop-up units for use in material handling equipment.

The manufacture and/or packaging of many types of commercial articles often involves the use of material handling equipment. One example of material handling equipment is a bench or workstation at which certain assembly or packaging steps for an article are performed. Another example of material handling equipment is a conveyor system for transporting an article from one workstation to another.

As can readily be appreciated, an article that is seated on top of a bench or workstation often must be repositioned or rotated thereon so that certain assembly or packaging steps can be performed. Similarly, it is often the case that the direction in which an article is traveling along a conveyor system must be altered or its movement altogether stopped. For these reasons, various types of repositioning devices and stopping devices have been devised that are adapted for use in material handling equipment.

One type of device that is adapted for use in material handling equipment is a pop-up unit, which is typically pneumatically-controlled. The pop-up unit is typically either in the form of a pop-up ball, which is designed to permit omnidirectional movement of an article thereon, or a pop-up stop, which is designed to impede or to prevent movement of an article thereon. Examples of various pneumatic pop-up units are disclosed in U.S. Pat. No. 6,516,934, inventor Masciarelli, which issued Feb. 11, 2003, and which is incorporated herein by reference. In one embodiment, the pneumatic pop-up unit comprises a stamped metal housing. The stamped metal housing is a generally cylindrical structure having an open top, a circular side wall, and a circumferential flange extending radially outwardly from the open top. A nipple is mounted in a bottom wall of the housing, the nipple being adapted for attachment to a pressurized gas supply. The pneumatic pop-up unit also comprises a stamped metal cap. The stamped metal cap includes an annular top wall, an inner side wall, and an outer side wall, the outer side wall being bent down across the outside edge of the flange and then radially inwardly against the bottom surface of the flange. The pneumatic pop-up unit additionally comprises a two-piece stamped metal piston slidably mounted within the housing and a stamped metal race disposed within the piston. The pneumatic pop-up unit further comprises a monolayer of ball bearings arranged within the race and a primary ball seated directly on top of the ball bearings, the primary ball being free to rotate in any direction. The primary ball is appropriately dimensioned so that its top extends through an open top of the piston. The pneumatic pop-up unit further comprises a rubber seal fitted around the piston and a coiled spring for biasing the piston downwardly within the housing. Typically, when the pneumatic pop-up unit is at rest, the coiled spring biases the piston downwardly within the housing such that the primary ball does not extend upwardly at all through the top of the cap. By contrast, when the pneumatic pop-up unit is actuated, pressurized gas is admitted into the housing through the nipple, causing the piston to move upwardly until the top of the primary ball extends through the top of the cap. In this manner, an article positioned on top of the unit is raised by and becomes seated on top of the primary ball.

Although the above-described pop-up unit has been found to be generally satisfactory for its intended purpose, the present inventor has noted some shortcomings in connection therewith. For example, once the internal components of the pop-up unit have been placed in the housing and the cap has been secured to the housing, the internal components of the pop-up unit, such as the primary ball, cannot be removed from the housing without removing the cap from the housing. However, removal of the cap from the housing is often cumbersome and/or may cause damage to the cap and/or the housing. This is unfortunate because the primary ball or other internal components of the unit can become worn and/or dirty over time. Consequently, the option most often employed is to replace the entire unit, as opposed to, for example, replacing a worn primary ball.

Another shortcoming noted by the present inventor is that the primary ball, because of its spherical shape, has very little surface area that actually comes into contact with the article being handled. As a result, because of the limited contact area between the primary ball and an article positioned thereon, it can be difficult at times to steer the article in a desired direction using the primary ball.

Still another shortcoming noted by the present inventor is that, over time, the rubber seal positioned around the piston tends to become worn. Such wear may be caused, for example, by the repeated sliding of the seal against the inner side wall of the housing as the piston is raised and lowered. As can be appreciated, the wearing of the seal may negatively impact the performance of the pop-up unit since leaks in or around the seal allow pressurized gas to escape from the housing, thereby making it more difficult to raise the piston when desired.

Besides pop-up units, another type of device that is adapted for use in material handling equipment is a unidirectional rotating support assembly, which is typically in the form of a roller or wheel. For example, in U.S. Pat. No. 6,401,900 B1, inventor Masciarelli, Jr. which issued Jun. 11, 2002, and which is incorporated herein by reference, there are disclosed various unidirectional rotating support assemblies adapted to be located in apertures provided in material handling equipment, such as the surface of a workstation, a scissors lift, a cart conveyor or the like. According to this patent, a unidirectional rotating support assembly typically includes a unidirectional rotating member, a support member and a rotating member support mechanism that rotatably supports the unidirectional rotating member with respect to the support member. The support member is configured or arranged so a portion thereof is received in the aperture in such a fashion that the support member has limited, if any, ability to move with respect to the work station surface. Thus, the rotating member also is maintained in a relatively fixed position with respect to the work surface. The support member includes an aperture therein, whose long axis is generally perpendicular to the work surface. The rotating member support mechanism is arranged so a portion thereof extends across this aperture or opening in the support member such that the unidirectional rotating member is disposed therein. The supporting mechanism in a particular embodiment is an axle and the unidirectional rotating member can be one of a wheel or a roller.

As noted above, the wheel or roller of the aforementioned unidirectional rotating support assembly is typically maintained in a fixed position above its respective work surface. Consequently, as compared to a pop-up unit, whose ball or stop may be raised and lowered as desired, the wheel or roller of the above-described unidirectional rotating support assembly is fixed in a raised position and cannot be lowered when repositioning or steering of an article is not desired. The present inventor has found this to be disadvantageous as the raised wheel or roller limits the amount of usable surface area of the work surface.

Other documents of interest may include the following, all of which are incorporated herein by reference: U.S. Pat. No. 6,457,865 B1, inventor Masciarelli, Jr., issued Oct. 1, 2002; U.S. Pat. No. 6,164,429, inventor Masciarelli, Jr., issued Dec. 26, 2000; U.S. Pat. No. 6,120,185, inventor Masciarelli, Jr., issued Sep. 19, 2000; U.S. Pat. No. 6,019,211, inventor Masciarelli, Jr., issued Feb. 1, 2000; U.S. Pat. No. 4,732,490, inventor Masciarelli, issued Mar. 22, 1988; U.S. Pat. No. 4,706,793, inventor Masciarelli, issued Nov. 17, 1987; U.S. Pat. No. 4,660,994, inventor Masciarelli, issued Apr. 28, 1987; and U.S. Pat. No. 4,627,526, inventor Masciarelli, issued Dec. 9, 1986.

SUMMARY OF THE INVENTION

It is an object of the present invention to provide a novel device for use in material handling equipment.

It is another object of the present invention to provide a device as described above that overcomes at least some of the shortcomings or disadvantages associated with existing devices for use in material handling equipment.

It is still another object of the present invention to provide a device as described above that can readily be mass-produced, that is easy to assemble, and that easily permits the replacement of certain components.

Therefore, according to one aspect of the invention, there is provided a pop-up wheel device for use in material handling equipment, the pop-up wheel device comprising: (a) a housing, the housing comprising a bottom wall, a side wall extending upwardly from said bottom wall, a flange extending outwardly from the top of the side wall, and an open top; (b) a cap, the cap being positioned on top of the housing and being secured to the flange of housing, the cap comprising an opening; (c) a piston, the piston being slidable within the housing between a lower position and an upper position; (d) a contact wheel, the contact wheel being freely rotatable in one direction and being coupled to the piston so that, when the piston is in the lower position, none of the contact wheel extends above the cap, and so that, when the piston is in the upper position, a portion of the contact wheel extends above the cap; and (e) a nipple, the nipple being mounted in the housing for use in transmitting fluid under pressure to and from said housing for use in sliding the piston between the lower position and the upper position.

In a more detailed feature of the invention, the contact wheel may be removable from the housing and/or insertable into the housing without removing the cap from the housing.

In a more detailed feature of the invention, the pop-up wheel device may further comprise means for biasing the piston towards the lower position.

In a more detailed feature of the invention, the biasing means may comprise a coiled spring.

In a more detailed feature of the invention, the pop-up wheel device may further comprise a seal, the seal may be fitted around the piston, and the seal may engage the side wall of the housing to create an air-tight chamber between the piston and the housing.

In a more detailed feature of the invention, the seal may have a split, the split may face downwardly, a first leg of the seal may engage the piston, and a second leg of the seal may engage the side wall of the housing.

In a more detailed feature of the invention, the housing may be made of zinc-coated galvanized steel.

In a more detailed feature of the invention, the pop-up wheel device may further comprise an axle, and the contact wheel may be rotatably mounted on the axle.

In a more detailed feature of the invention, the pop-up wheel device may further comprise a wheel mount, the contact wheel may be rotatably mounted on the wheel mount, and the wheel mount may be coupled to the piston.

According to another aspect of the invention, there is provided a pop-up wheel device for use in material handling equipment, the pop-up wheel device comprising: (a) a housing, the housing comprising a bottom wall, a side wall extending upwardly from said bottom wall, a flange extending outwardly from the top of the side wall, and an open top; (b) a cap, the cap being positioned on top of the housing and being secured to the flange of housing, the cap comprising an opening; (c) a piston, the piston being slidable within the housing between a lower position and an upper position; (d) a nipple, the nipple being mounted in the housing for use in transmitting fluid under pressure to and from said housing for use in sliding the piston between the lower position and the upper position; (e) a spring for biasing the piston towards the lower position; (f) a wheel mount, the wheel mount being seated on the piston; and (g) a wheel assembly, the wheel assembly being coupled to the wheel mount and comprising a contact wheel, the contact wheel being freely rotatable in one direction, wherein, when the piston is in the lower position, none of the contact wheel extends above the cap, and wherein, when the piston is in the upper position, a portion of the contact wheel extends above the cap.

In a more detailed feature of the invention, the housing may have a non-circular transverse cross-section.

In a more detailed feature of the invention, the wheel assembly may be removable from the housing and/or insertable into the housing without removing the cap from the housing.

In a more detailed feature of the invention, the pop-up wheel device may further comprise a seal, the seal may be fitted around the piston, and the seal may engage the side wall of the housing to create an air-tight chamber between the piston and the housing.

In a more detailed feature of the invention, the housing may be made of zinc-coated galvanized steel.

In a more detailed feature of the invention, the piston may comprise a bottom wall, a lower side wall extending from the bottom wall, a shelf extending from the lower side wall, an upper side wall extending from the shelf, and an open top. In addition, when viewed from above, the upper side wall may be longer and wider than the lower side wall, with the shelf extending generally horizontally between the top of the lower side wall and the bottom of the upper side wall. In addition, the bottom wall may slope upwardly and then curve slightly downwardly as one moves inwardly from a periphery of the bottom wall, thereby defining a track-shaped recess spaced inwardly from the periphery of the bottom wall.

In a more detailed feature of the invention, the wheel mount may comprise a first member, the first member may be seated on the bottom wall of the piston and may comprise a bottom, a side, a top, and a cavity extending downwardly from the top, and the first member may be shaped to include at least one resilient protrusion extending into the cavity for removably snap-locking in place the wheel assembly.

In a more detailed feature of the invention, the wheel mount may further comprise a second member, the second member may be inserted over a portion of the first member and may comprise a top wall, a side wall extending downwardly from the top wall, a peripheral flange extending outwardly from a bottom of the side wall, and an open bottom, and the peripheral flange of the second member may be seated on the shelf of the piston.

In a more detailed feature of the invention, the wheel assembly may further comprise an axle, and the contact wheel may be rotatably mounted on the axle.

According to another aspect of the invention, there is provided a pop-up wheel device for use in material handling equipment, the pop-up wheel device comprising: (a) housing, the housing comprising a bottom wall, a side wall extending upwardly from said bottom wall, a flange extending outwardly from the top of the side wall, and an open top; (b) a cap, the cap being positioned on top of the housing and being secured to the flange of housing, the cap comprising an opening; (c) a piston, the piston being slidable within the housing between a lower position and an upper position, the piston comprising a bottom wall, a lower side wall extending upwardly from the bottom wall, a shelf extending outwardly from a top of the lower side wall, and an upper side wall extending upwardly from an outer periphery of the shelf; (d) a seal, the seal being fitted around the lower side wall of the piston and engaging the side wall of the housing to create an air-tight chamber between the piston and the housing; (e) a nipple, the nipple being mounted in the housing for use in transmitting fluid under pressure to and from said housing for use in sliding the piston between the lower position and the upper position; (f) a spring for biasing the piston towards the lower position; (g) a wheel mount, the wheel mount comprising a first member and a second member, the first member being seated on the bottom wall of the piston and comprising a bottom, a side, a top, and a cavity extending downwardly from the top, the second member being inserted over a portion of the first member and comprising a top wall, a side wall extending downwardly from the top wall, a peripheral flange extending outwardly from a bottom of the side wall, and an open bottom, the peripheral flange of the second member being seated on the shelf of the piston; and (h) a wheel assembly, the wheel assembly comprising an axle and a contact wheel, the axle being disposed within the cavity of the first member of the wheel mount, the contact wheel being freely rotatable in one direction on the axle, a portion of the contact wheel extending above the wheel mount, wherein, when the piston is in the lower position, none of the contact wheel extends above the cap, and wherein, when the piston is in the upper position, a portion of the contact wheel extends above the cap.

In a more detailed feature of the invention, the wheel assembly may be removable from the housing and/or may be insertable into the housing without removing the cap from the housing.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numerals represent like parts:

FIGS. 4(a) through 4(d) are perspective, top, end, and longitudinal section views, respectively, of the housing shown in FIG. 2;

DETAILED DESCRIPTION OF THE INVENTION

Figure 1:
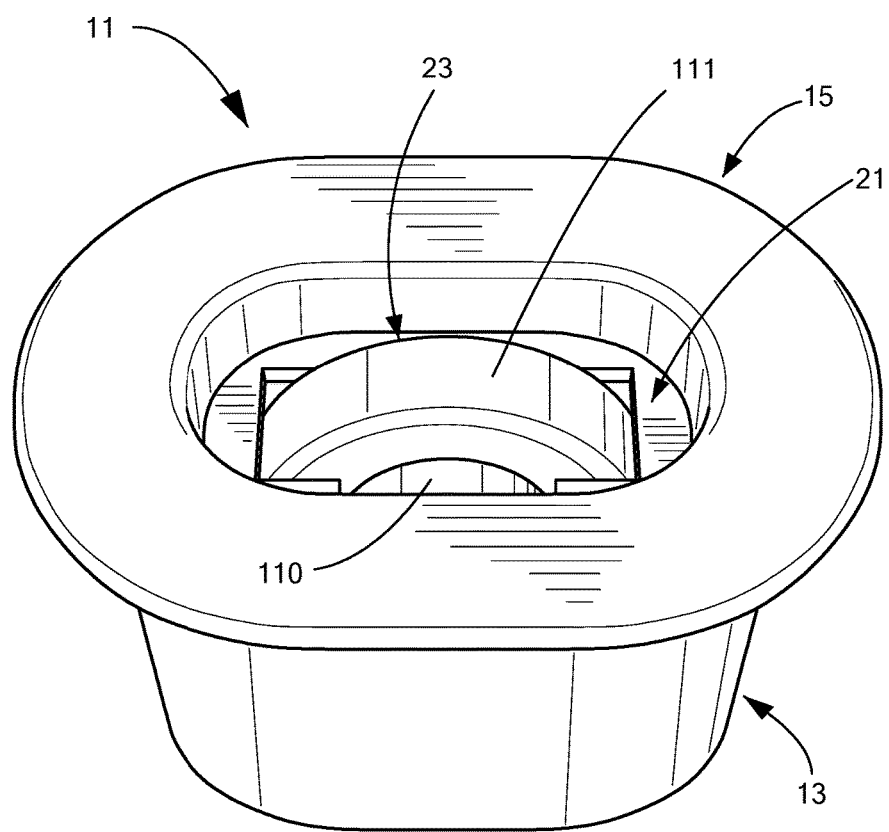
FIG. 1 is a perspective view of one embodiment of a pop-up wheel device constructed according to the present invention, the pop-up wheel device being shown in a retracted position.
Figure 2:
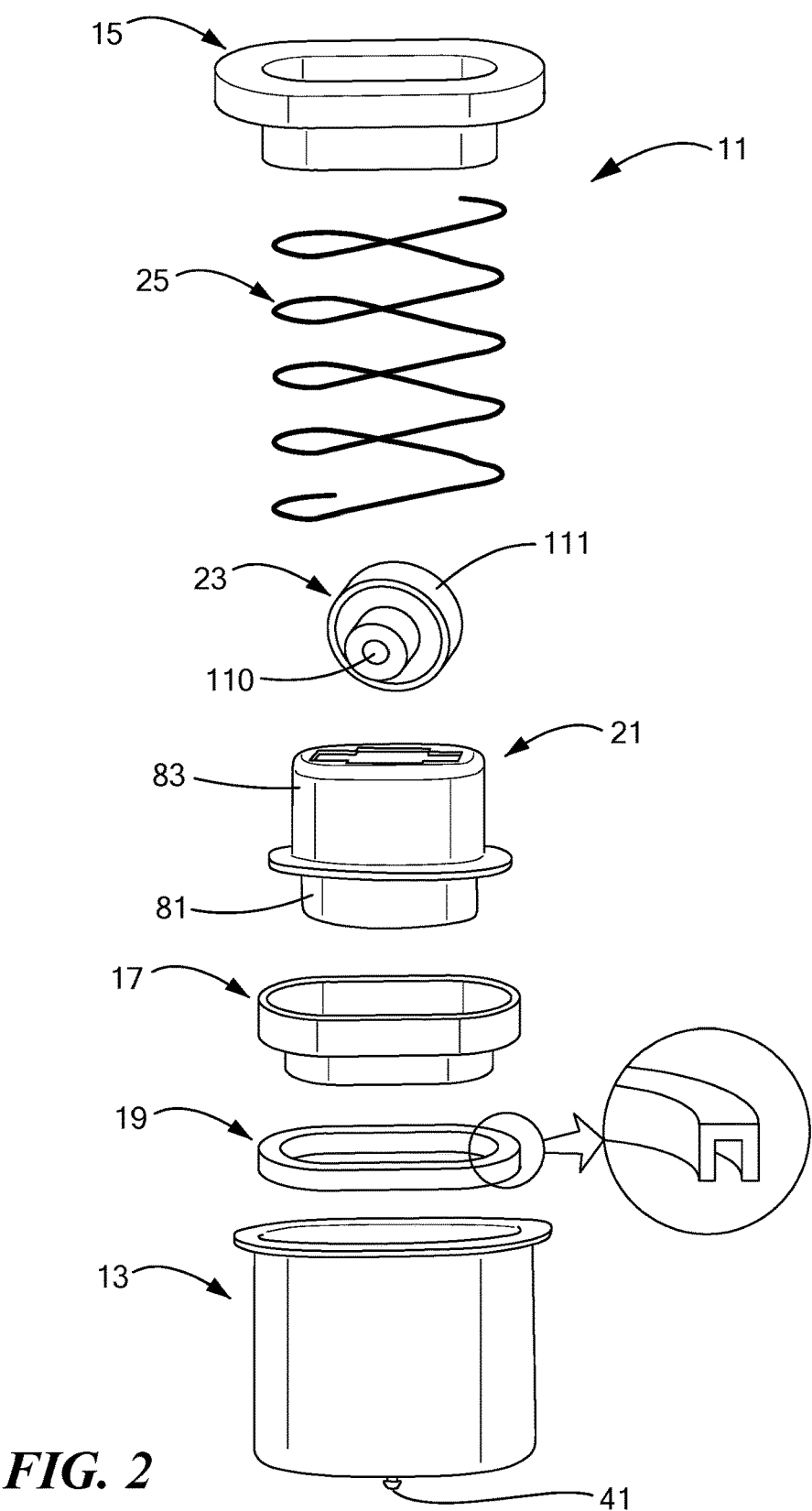
FIG. 2 is a partly exploded perspective view of the pop-up wheel device shown in FIG. 1.
Figure 3A:
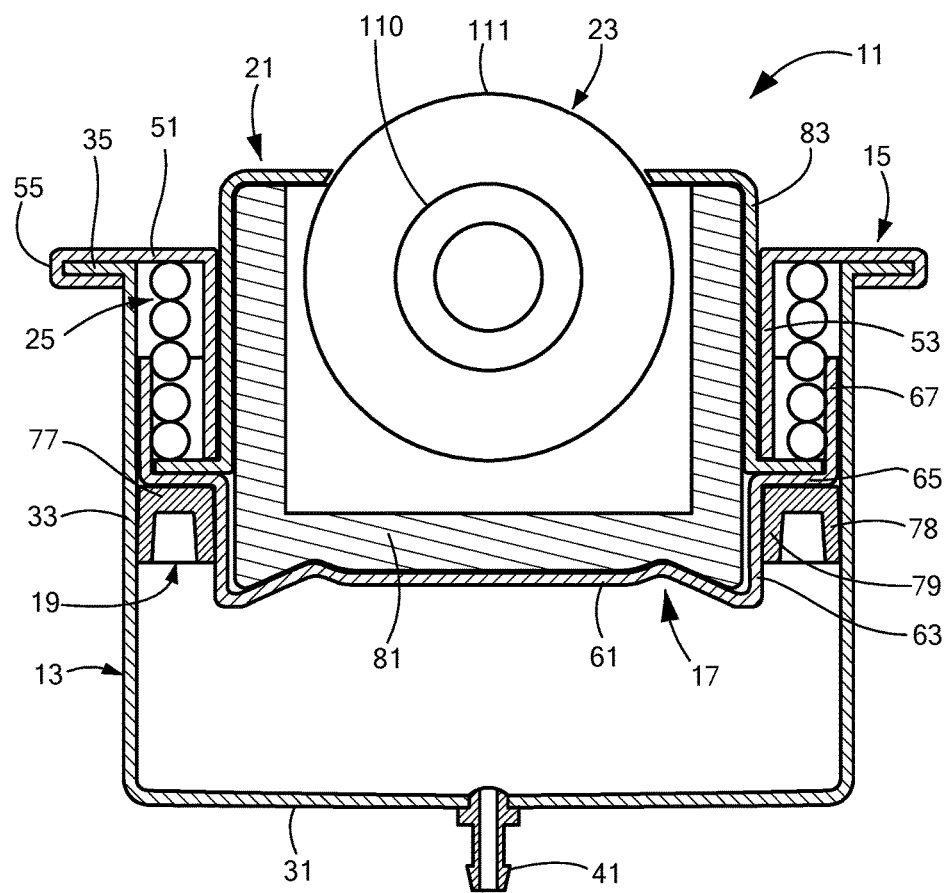
FIGS. 3(a) and 3(b) are simplified longitudinal section views of the pop-up wheel device shown in FIG. 1, the pop-up wheel device being shown in an extended position and in a retracted position, respectively.
Figure 3B:
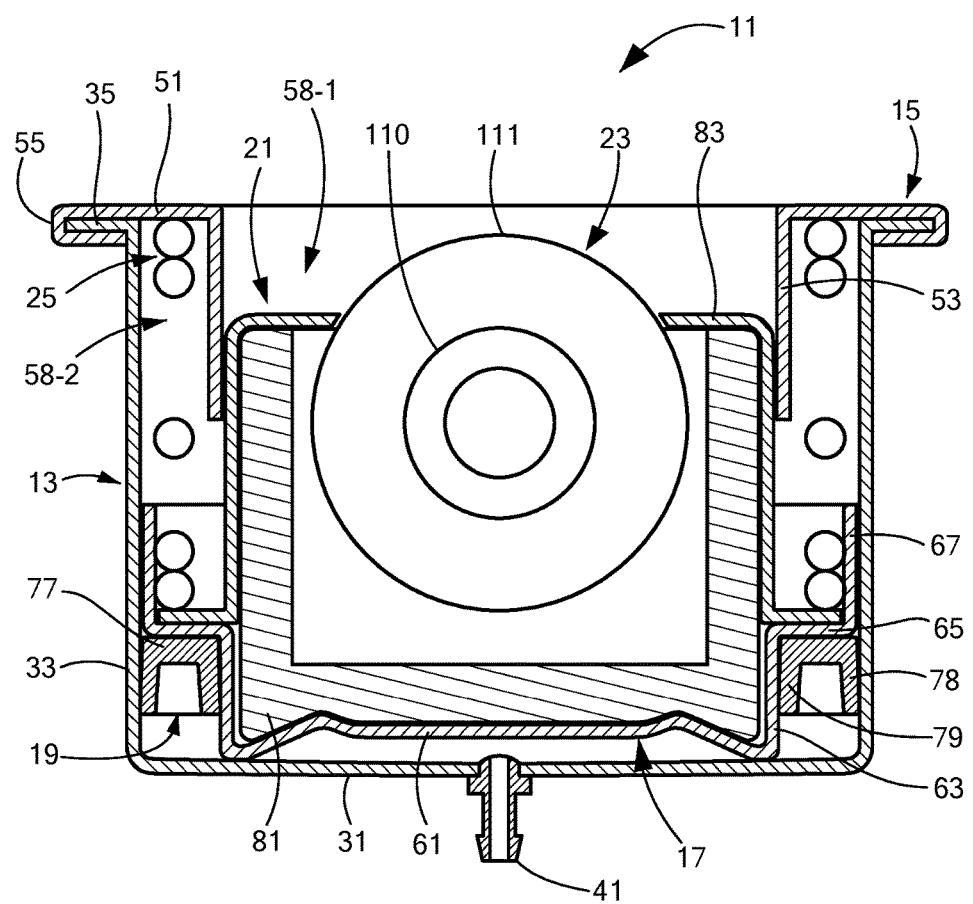
Figure 5A:
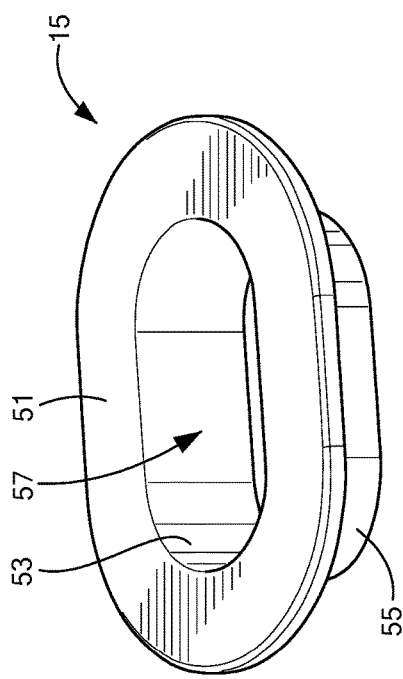
FIGS. 5(a) through 5(d) are perspective, top, end, and longitudinal section views, respectively, of the cap shown in FIG. 2.
Figure 5B:
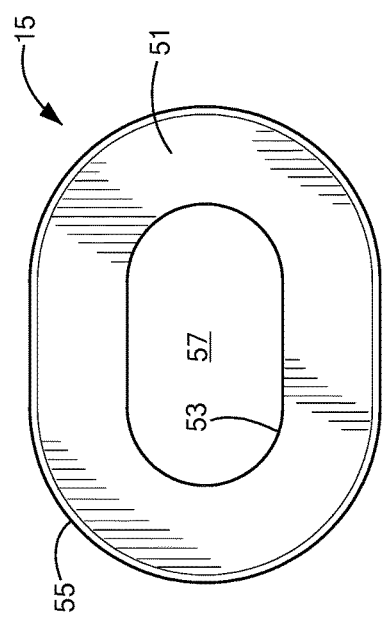
Figure 5C:
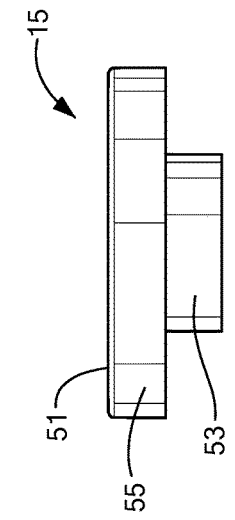
Figure 5D:
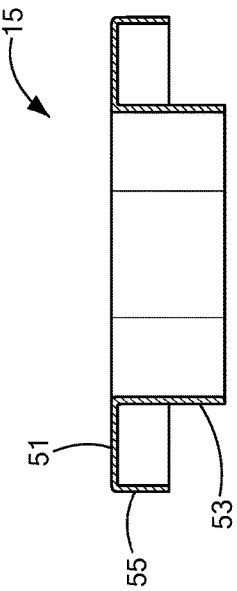
Figure 6A:
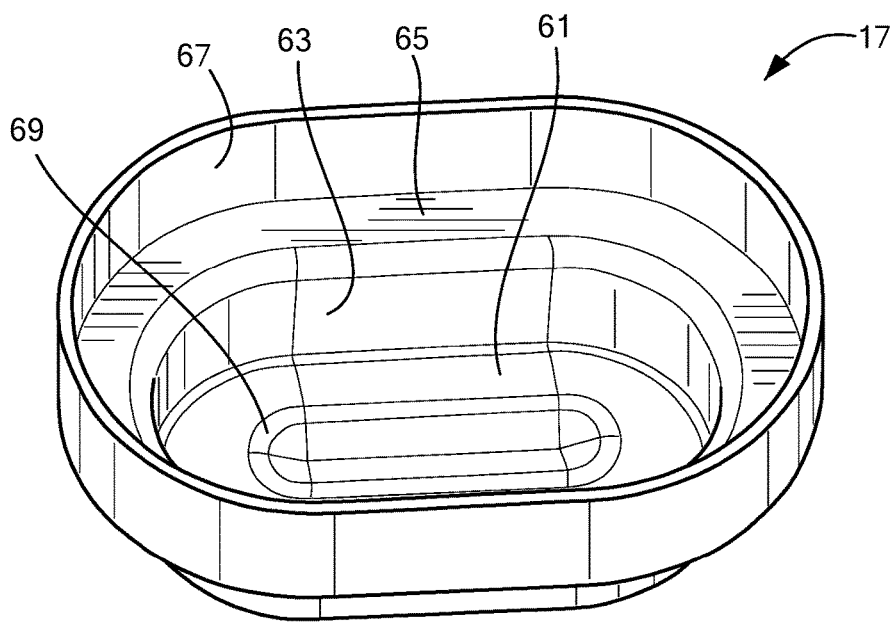
FIGS. 6(a) through 6(d) are top perspective, bottom perspective, longitudinal cross-section, and lateral cross-section views, respectively, of the piston shown in FIG. 2.
Figure 6B:
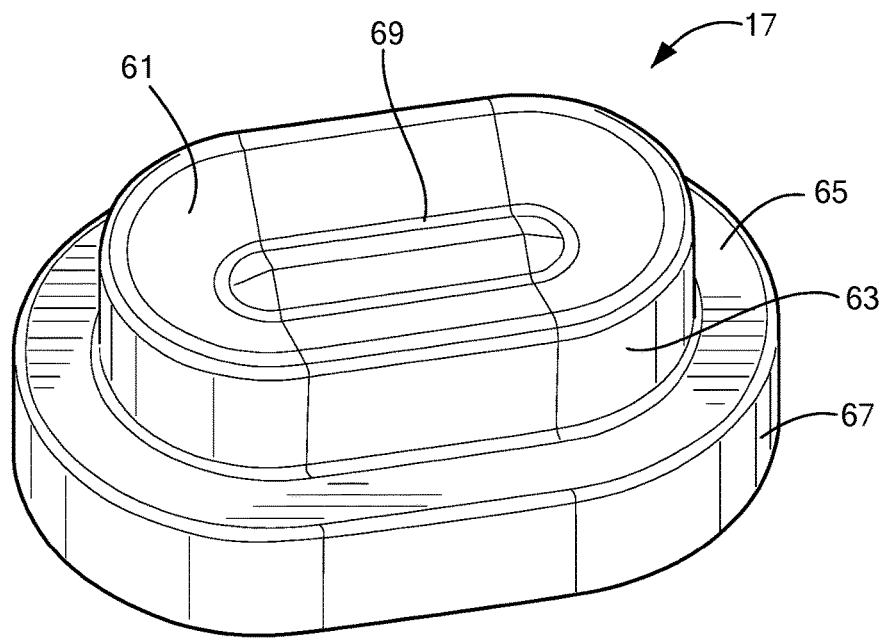
Figure 6C:
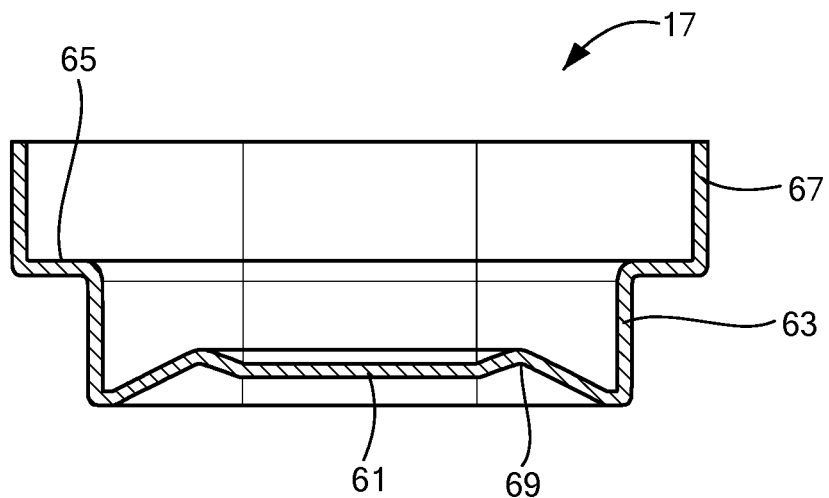
Figure 6D:
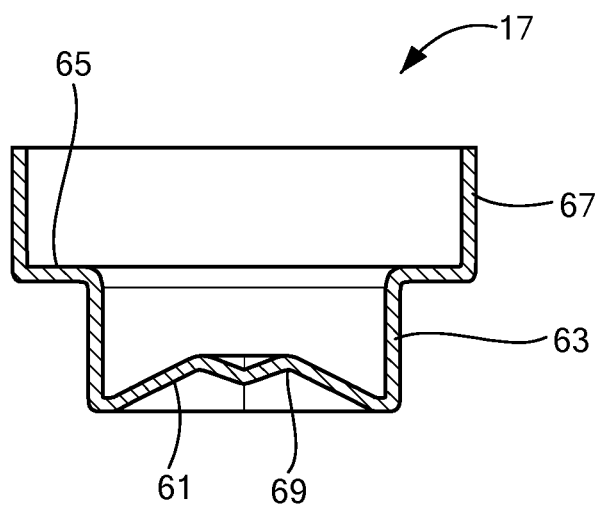

Referring now to FIGS. 1, 2, 3(a), and 3(b), there are shown various views of one embodiment of a pop-up wheel device that is suitable for use in material handling equipment, the pop-up wheel device being constructed according to the present invention and being represented generally by reference numeral 11. For clarity, certain details of pop-up wheel device 11 that are discussed elsewhere in this application or that are not critical to an understanding of the invention may not be shown in one or more of FIGS. 1, 2, 3(a), and 3(b) or may be shown therein in a simplified manner.

Pop-up wheel device 11 may comprise a housing 13, a cap 15, a piston 17, a seal 19, a wheel mount 21, a wheel assembly 23, and a coiled spring 25.

Housing 13, which is also shown separately in FIGS. 4(*a*) through 4(*d*), may comprise a generally hollow container or can having a track-shaped transverse cross-section, i.e., two generally parallel straight sides and two opposed curved ends. Instead of having a track-shaped transverse cross-section, housing 13 may have other types of transverse cross-sections. For example, housing 13 may have an oval transverse cross-section, an elliptical transverse cross-section, or any other type of non-circular transverse cross-section that corresponds generally to the shape of a wheel mounted in housing 13 or that can accommodate such a wheel. Housing 13 may be shaped to include a bottom wall 31, a side wall 33 extending upwardly from bottom wall 31, a peripheral flange 35 extending radially outwardly from the top of side wall 33, and an open top.

Housing 13 may be a one-piece structure that may be made by a process comprising, for example, drawing or stamping a sheet of a suitably strong material, such as a sheet of galvanized steel. After being drawn or stamped, the galvanized steel of housing 13 may be treated with a suitable coating. For example, such a coating may be a thin layer of zinc, which may be, for example, 1-2 mils in thickness, and which may be applied to the galvanized steel of housing 13, for example, by electroplating.

The aforementioned zinc coating may provide multiple benefits. For example, the zinc coating may reduce corrosion of the galvanized steel of housing 13. Moreover, the zinc coating may make the galvanized steel surface of housing 13 more uniform and, consequently, less rough. More specifically, the galvanized steel of housing 13, prior to the application thereto of the zinc coating, typically has a certain surface roughness due to small variations, i.e., peaks and valleys, in its surface. By coating the surface of the galvanized steel of housing 13, these variations may be minimized, thereby reducing the surface roughness of the galvanized steel of housing 13. One benefit of the aforementioned reduction in surface roughness of the galvanized steel of housing 13 may be a reduction in friction between housing 13 and seal 19, seal 19 repeatedly sliding against the inside surface of side wall 33 of housing 13 when pop-up wheel device 11 is in use. As a result of the reduction in friction between housing 13 and seal 19, seal 19 may experience less wear and may be better able to maintain fluid pressure within housing 13, which may result in better sustained performance for pop-up wheel device 11. Moreover, by zinc-coating the galvanized steel of housing 13, one may obscure imperfections in the galvanized steel of housing 13 that may have been introduced during the drawing or stamping process. (For example, if, for some reason, there is a residue on a punch or die used to make housing 13, this may transfer onto housing 13 as a scratch or void thereon. Such scratches or voids may be filled, at least in part, by the zinc coating.)

A nipple 41 may be mounted within an opening 42 in bottom wall 31 of housing 13. Although nipple 41 is shown centered in bottom wall 31, it should be understood that nipple 41 may be positioned off-center in bottom wall 31. Nipple 41, which may be made, for example, of brass or another suitably durable material, may be adapted for connection to a pressurized fluid supply so that, as desired, fluid may be delivered into housing 13 (for example, to raise piston 17) or may be withdrawn from housing 13 (for example, to lower piston 17). Said pressurized fluid supply may be a pressurized gas supply, typically in the form of a pneumatic cylinder, or may be a pressurized liquid supply, typically in the form of a hydraulic cylinder. In the case of a pressurized liquid supply, oil is typically a more preferred liquid than water as it is less likely to cause corrosion of the components within housing 13.

Cap 15, which is also shown separately in FIGS. 5(*a*) through 5(*d*), may be a one-piece structure that may be made, for example, by drawing or stamping a sheet of a suitably strong material. For example, cap 15 may be made by a process that comprises drawing or stamping a sheet of galvanized steel, which, like housing 13, may be coated, after being drawn or stamped, with a zinc coating of approximately 1-2 mil. Cap 15 may comprise a top wall 51, an inner side wall 53, and an outer side wall 55. Top wall 51 may be flat and generally track-shaped and may define a generally track-shaped opening 57 centered therewithin. Inner side wall 53, which may also be generally track-shaped, may extend downwardly from the inner periphery of top wall 51. Inner side wall 53, whose outer dimension is somewhat smaller than the inner dimension of housing 13, may partially subdivide housing 13 into inner and outer track-shaped chambers 58-1 and 58-2, respectively. Outer side wall 55, which may also be generally track-shaped, may extend downwardly from the outer periphery of top wall 51 across the outside edge of flange 35 and may be bent inwardly towards inner side wall 53 while pressed against the bottom surface of flange 35. When cap 15 is manufactured, outer side wall 55 is typically not bent and, in fact, preferably extends straight down from top wall 51. However, after cap 15 and housing 13 are brought together, outer side wall 55 may be bent peripherally around flange 35 in the above manner to secure cap 15 to housing 13.

Piston 17, which is also shown separately in FIGS. 6(*a*) through 6(*d*), may be a one-piece, hollow container of generally track-shaped transverse cross-section. Piston 17 may be disposed within housing 13 in such a way as to be adapted for sliding movement up and down therewithin. Piston 17 may be made, for example, by a process that comprises drawing or stamping a sheet of a suitably strong material. For example, piston 17 may be made by drawing or stamping a sheet of galvanized steel, which, like housing 13 and cap 15, may be coated, after being drawn or stamped, with a zinc coating of approximately 1-2 mil. Piston 17 may be shaped to include a bottom wall 61, a lower side wall 63, a shelf 65, an upper side wall 67, and an open top. Both lower side wall 63 and upper side wall 67 may be track-shaped. When viewed from above, upper side wall 67 may be longer and wider than lower side wall 63, with shelf 65 extending generally horizontally between the top of lower side wall 63 and the bottom of upper side wall 67. Upper side wall 67 may have an outer dimension that is just slightly less than the inner dimension of side wall 33 of housing 13.

Bottom wall 61 of piston 17 may be shaped to direct the flow of fluid that enters housing 13 from nipple 41 to desired areas of bottom wall 61. For example, in the present embodiment, bottom wall 61 slopes upwardly and then curves slightly downwardly as one moves inwardly from the periphery of bottom wall 61, thereby defining a track-shaped recess 69 spaced inwardly from the periphery of bottom wall 61. In this way, as fluid enters housing 13 from nipple 41, said fluid is distributed throughout recess 69, resulting in a more uniform flow of fluid used to raise piston 17. By contrast, if bottom wall 61 were flat, fluid entering housing 13 from nipple 41 would flow to wherever the path of least resistance is located, thereby making the movement of piston 17 more erratic and harder to control.

Figure 7A:
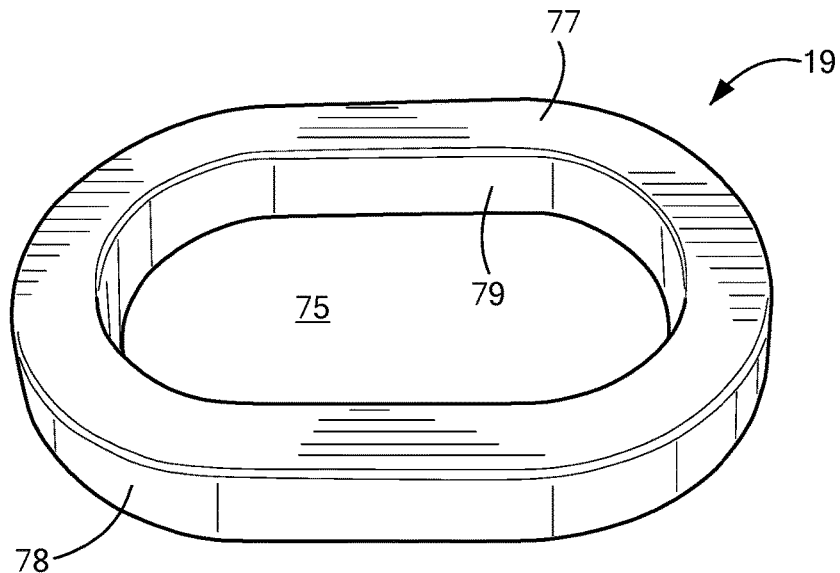
FIGS. 7(a) and 7(b) are top perspective and bottom perspective views, respectively, of the seal shown in FIG. 2.
Figure 7B:
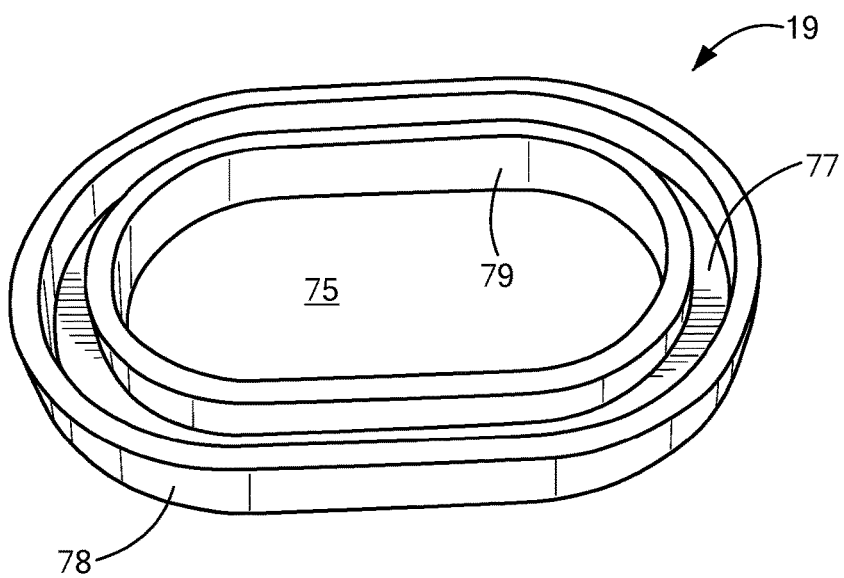
Figure 8A:
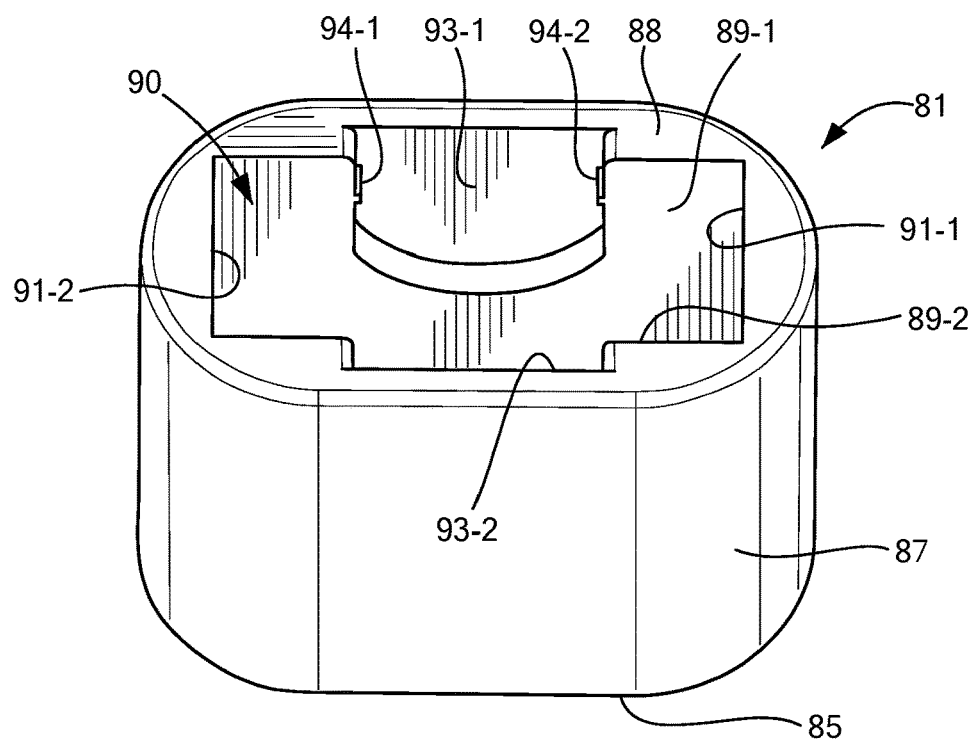
FIGS. 8(a) through 8(d) are top perspective, bottom perspective, top, and lateral section views, respectively, of the first member of the wheel mount shown in FIG. 2.
Figure 8B:
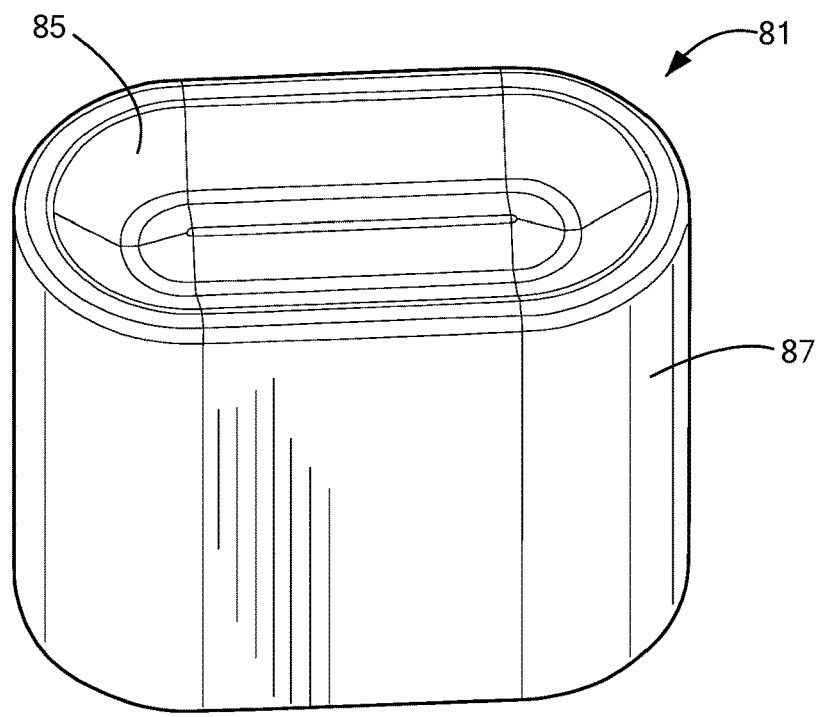
Figure 8C:
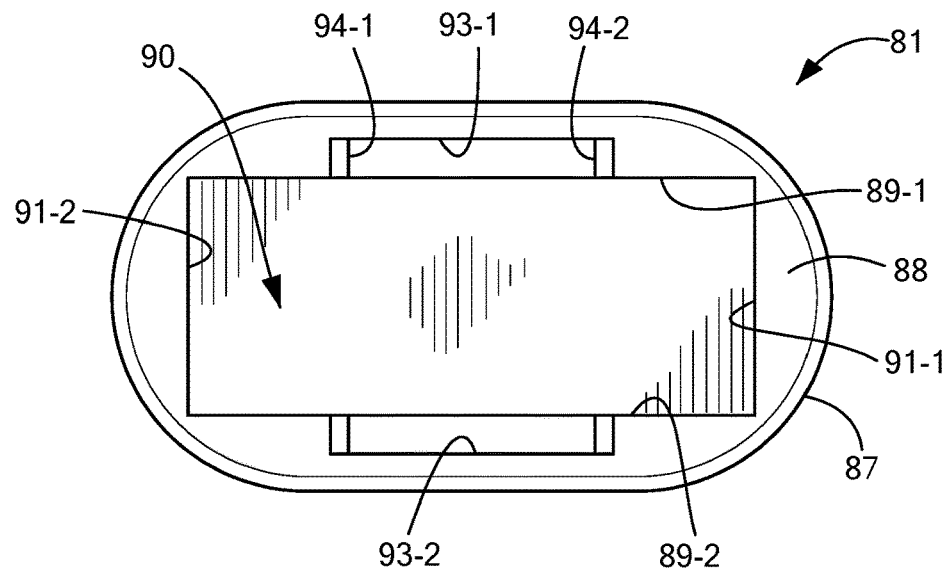
Figure 8D:
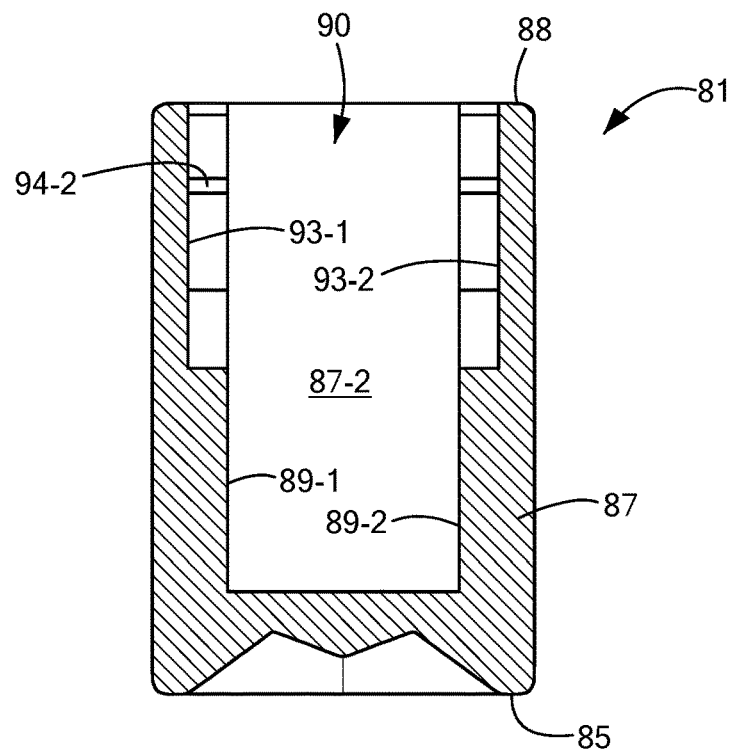

Seal 19, which is also shown separately in FIGS. 7(*a*) and 7(*b*), may be a one-piece, generally track-shaped structure having a central, track-shaped opening 75. Seal 19, which may be made, for example, of rubber or another similarly suitable material, may be snugly fitted around the outer surface of lower side wall 63 of piston 17 and may engage, at its top surface 77, the bottom surface of shelf 65 of piston 17 so as to keep seal 19 from sliding up on piston 17. Seal 19 may be used to create an air-tight chamber between lower side wall 63 piston 17 and housing 13. Seal 19 is preferably of the split-design variety (e.g., U-cup, block-V), with the split facing downwardly, so that, when seal 19 is subjected to upward fluid pressure, its outer leg 78 is urged outwardly against the inside surface of wall 33 of housing 13 and its inner leg 79 is urged inwardly against the outside of lower side wall 63 of piston 17. Although less preferred, seal 19 may be a track-shaped O-ring or the like.

Wheel mount 21 may comprise a first member 81 and a second member 83. First member 81, which is also shown separately in FIGS. 8(*a*) through 8(*d*), may comprise a block of generally track-shaped transverse cross-section that includes a bottom 85, a side 87, and a top 88. First member 81 may be a one-piece structure made, for example, by injection-molding a suitable polymer. The bottom surface of bottom 85, which is adapted to be seated on top of bottom wall 61 of piston 17, may be shaped complementarily to bottom wall 61 of piston 17. A generally rectangular prismatic cavity 90 may be provided in first piece 81 and may extend downwardly from top wall 88 to a depth short of bottom 85. Cavity 90 may be bound, in part, by a pair of side surfaces 89-1 and 89-2 and a pair of end surfaces 91-1 and 91-2. Recesses 93-1 and 93-2, which may extend downwardly a short distance from the top of cavity 90, may be formed in side surfaces 89-1 and 89-2, respectively, and may be used to mount wheel assembly 23. As can be seen, for example, in FIG. 8(*a*), side surface 89-1 may be shaped to include a pair of protrusions 94-1 and 94-2 that extend into recess 93-1. During the assembly of pop-up wheel device 11, as an axle of wheel assembly 23 is pushed down into prismatic cavity 90, protrusions 94-1 and 94-2 may be temporarily pushed away from each other by said axle of wheel assembly 23; then, after the axle of wheel assembly 23 has been inserted past protrusions 94-1 and 94-2, protrusions 94-1 and 94-2 may resiliently return to their original positions, thereby snap-locking the axle, and, as a result, wheel assembly 23, into place relative to first member 81. (Side surface 89-2 may be similarly shaped to include a corresponding pair of protrusions that extend into recess 93-2 and that may be used to snap-lock the opposite end of axle into recess 93-2.) Thereafter, if it is desired to remove wheel assembly 23 from first member 81, one may force wheel assembly 23 upwardly relative to first member 81 sufficiently to cause the axle to be moved past protrusions 94-1 and 94-2. This may be done, for example, by pulling wheel assembly 23 away from first member 81 using a pair of pliers or by prying wheel assembly 23 away from first member 81 using a flat-head screwdriver.

Figure 9A:
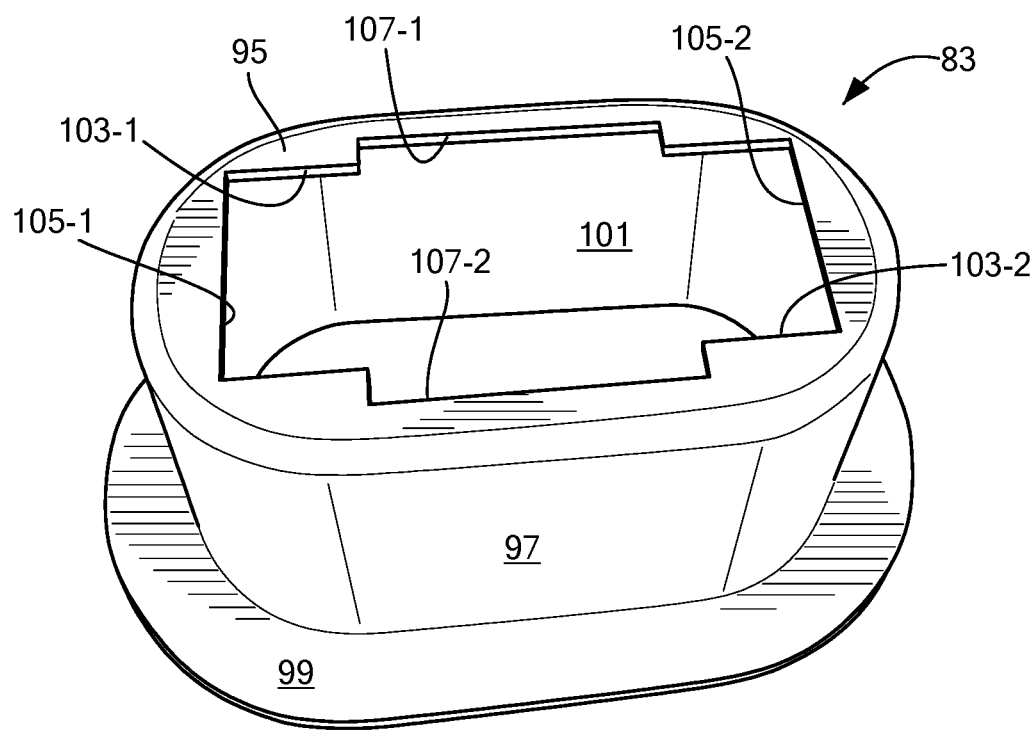
FIGS. 9(a) and 9(b) are top perspective and bottom perspective views, respectively, of the second member of the wheel mount shown in FIG. 2.
Figure 9B:
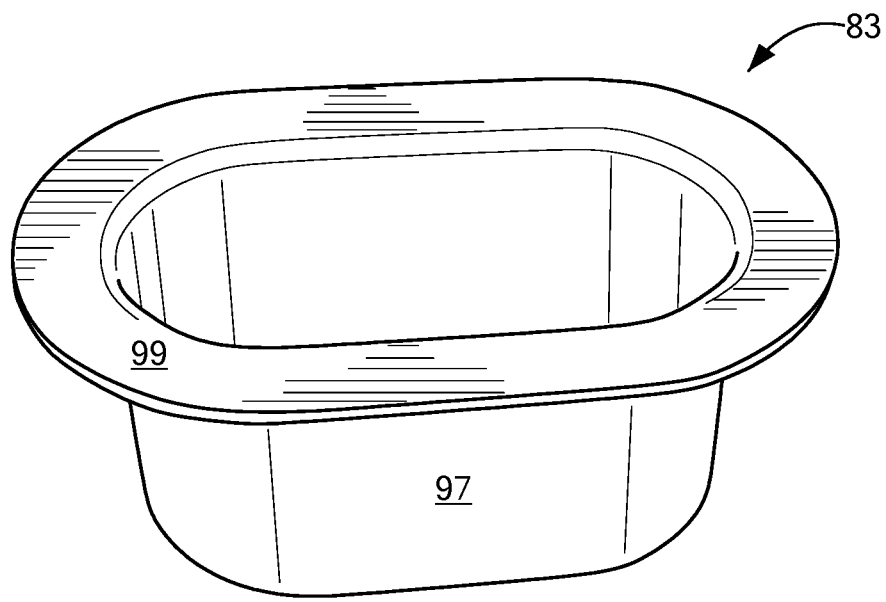

Second member 83, which is also shown separately in FIGS. 9(*a*) and 9(*b*), may be a one-piece, hollow structure of generally track-shaped transverse cross-section. Second member 83 may be shaped to include a top wall 95, a side wall 97 extending downwardly from top wall 95, a peripheral flange 99 extending outwardly from the bottom of side wall 97, and an open bottom. An opening 101 may be provided in top wall 95 of second member 83. Opening 101 may be shaped to correspond to the top of prismatic cavity 90 of first member 81. Accordingly, opening 101 may be bounded by a pair of sides 103-1 and 103-2 and a pair of ends 105-1 and 105-2, with side 103-1 having a recess 107-1 and with side 103-2 having a recess 107-2. Second member 83 may be made, for example, by drawing or stamping a sheet of a suitably strong material, such as galvanized steel, which may thereafter be coated with a zinc-coating of approximately 1-2 mil.

Second member 83 may be fixedly mounted, for example, by a friction-fit, over the top of first member 81, with a lower portion of first member 81 extending downwardly beyond peripheral flange 99 of second member 83. Preferably, first member 81 and second member 83 are appropriately dimensioned so that wheel mount 21 may be seated within and transported by piston 17, with peripheral flange 99 being seated upon shelf 65 of piston 17 and with bottom 85 of first member 81 being seated upon bottom wall 61 of piston 17. In this manner, as piston 17 is raised or lowered, wheel mount 21 is correspondingly raised or lowered. Where second member 83 is made of a material like zinc-coated galvanized steel, second member 83 may protect first member 81 from wear, particularly where first member 81 may be made of molded plastic.

As noted above, first member 81 of wheel mount 21 may be made, for example, by injection molding a suitable polymer whereas second member 83 of wheel mount 21 may be made, for example, by drawing or stamping a metal sheet, such as a galvanized steel sheet. Such a two-piece construction is advantageous since features like protrusions 94-1 and 94-2 can more easily be made by injection molding than by machining or stamping metal. At the same time, the fabrication of second member 83 by drawing or stamping a metal sheet endows wheel mount 21 with a far superior strength than could be achieved by injection molding alone.

Figure 11:
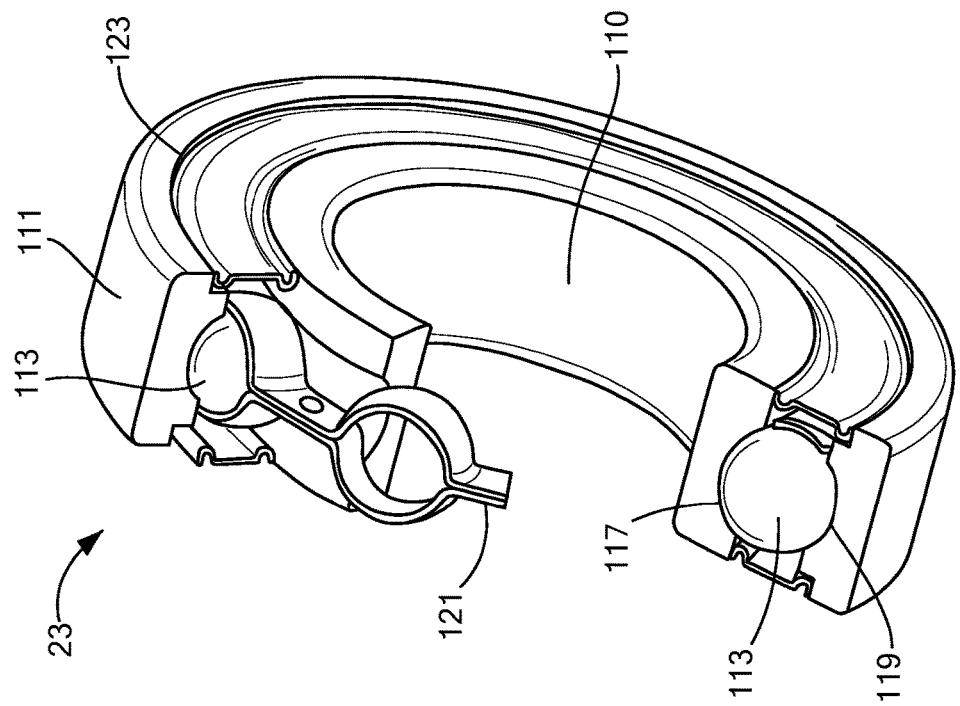
FIG. 11 is a section view, broken away in part, of the wheel assembly shown in FIG. 10, the axle of the wheel assembly being shown axially truncated.
Figure 10:
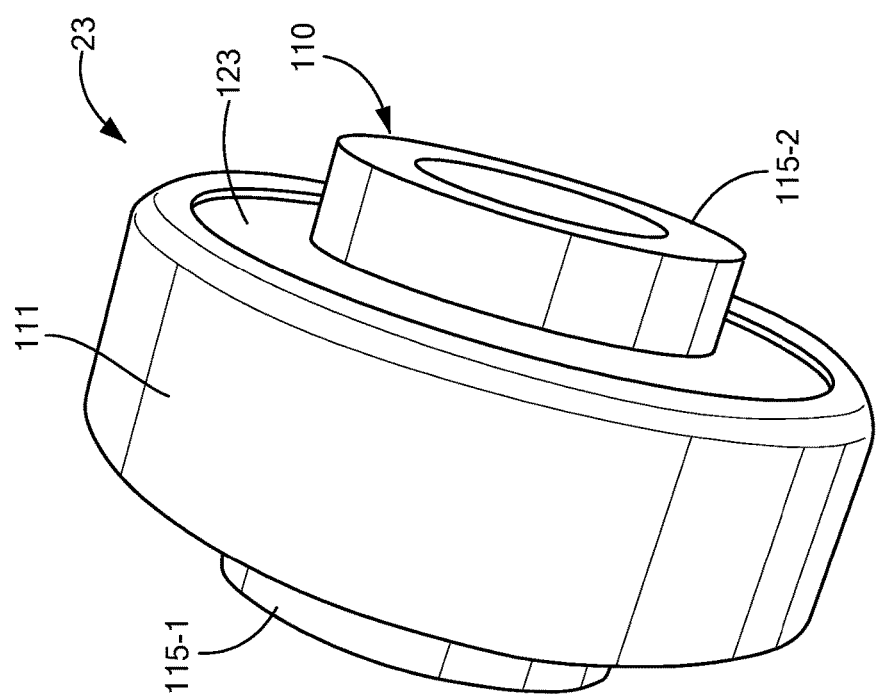
FIG. 10 is a perspective view of the wheel assembly shown in FIG. 2.

Wheel assembly 23, which is also shown separately in FIGS. 10 and 11, may be in the form of a ball bearing. Wheel assembly 23 may comprise an axle 110, a unidirectional contact wheel 111, and a plurality of balls 113. Axle 110, which may serve as a stationary element, may be a hollow cylindrical structure that is appropriately dimensioned so that its ends 115-1 and 115-2 may be mounted in the manner described above within recesses 93-1 and 93-2, respectively of first member 81. A groove 117 may be provided along the outer periphery of axle 110 and may be used to receive balls 113. Wheel 111, which may serve as a rotating element, may be an annular structure concentrically placed around axle 110 and having a groove 119 along its inner periphery used to receive balls 113. Without wishing to be limited to any particular dimensions of wheel 111, wheel 111 preferably has a diameter that is greater than its width. For example, wheel 111 may have a diameter of approximately ⅞ inch and a width of approximately ¼ inch. Wheel 111 is preferably dimensioned so that, when axle 110 is mounted within recesses 93-1 and 93-2, wheel 111 is free to rotate, with approximately one-half of wheel 111 being disposed within cavity 90 and the remainder extending above cavity 90. Wheel assembly 23 may further comprise one or more brackets 121 for maintaining the spacing between balls 113 and a casing 123 for covering balls 113 and brackets 121.

Figure 12:
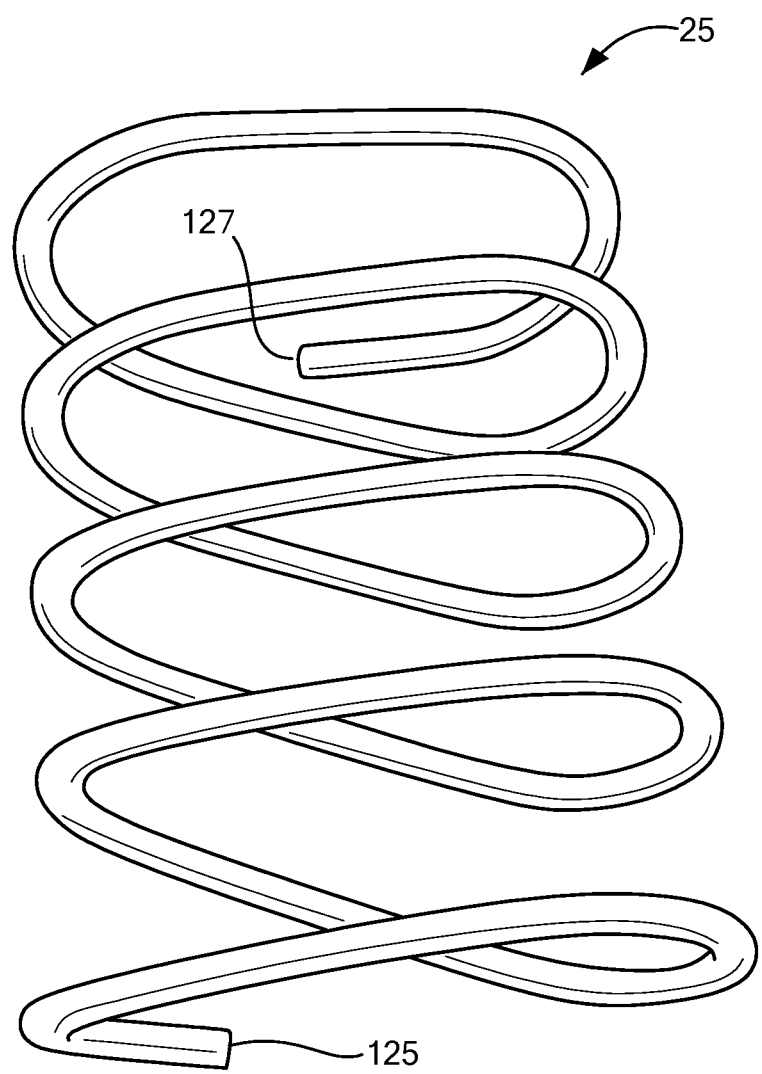
FIG. 12 is a perspective view of the coiled spring shown in FIG. 2.

Coiled spring 25, which is also shown separately in FIG. 12, may be made, for example, of zinc-coated galvanized steel and may have a track-shaped profile when viewed from either of its opposed ends. Coiled spring 25 may be used to bias piston 17 downwardly within housing 13 so that, when the fluid pressure within housing 13 is reduced, piston 17 returns to its lowered position. Coiled spring 25 may comprise a first end 125 and a second end 127. First end 125 may be seated on top of peripheral flange 99 of second member 83, and second end 127 may abut the bottom surface of top wall 51 of cap 15.

One possible method for assembling pop-up wheel device 11 may be as follows: First, wheel assembly 23 may be joined to wheel mount 21, for example, by inserting wheel assembly 23 into cavity 90 until the ends 115-1 and 115-2 of axle 110 are secured within recesses 93-1 and 93-2, respectively. Then, wheel mount 21 may be placed within piston 17, and seal 19 may be attached to lower portion of piston 17. Next, the combination of piston 17, seal 19, wheel mount 21, and wheel assembly 23 may be positioned within housing 13. Next, first end 125 of coiled spring 25 may be seated on top of peripheral flange 99 of second member 83. Next, cap 15 may be placed on top of second end 127 of coiled spring 25, and cap 15 may be secured to housing 13.

In use, to raise wheel 111, pressurized fluid may be admitted into housing 13 using nipple 41. This may cause piston 17 to move upwardly within housing 13, overcoming the downwardly biasing force of coiled spring 25 and causing the compression of coiled spring 25. The upward movement of piston 17, in turn, may cause wheel mount 21 and wheel assembly 23, both of which are carried by piston 17, to similarly move upwardly relative to housing 13. In its fully extended or raised position (as seen, for example, in FIG. 3(*a*)), approximately one-half of wheel 111 may extend above the top surface of cap 15. Thereafter, to lower wheel 111, pressurized fluid may be removed from housing 13 using nipple 41. As a result, coiled spring 25 may bias piston 17 downwardly within housing 13, thereby causing wheel mount 21 and wheel assembly 23 to be lowered. In its fully retracted or lowered position (as seen, for example, in FIG. 3(*b*)), wheel 111 may be positioned entirely below the top surface of cap 15.

As noted above, one advantageous feature of pop-up wheel device 11 is that wheel assembly 23 may be removed and, if desired, replaced without removing cap 15 from housing 13. This may be done, for example, by operating pop-up wheel device 11 so that wheel 111 is placed in its raised position and then, with wheel 111 thus raised, detaching wheel assembly 23 from wheel mount 21, for example, using pliers or a flat-head screwdriver. The same or a different wheel assembly 23 may thereafter be attached to wheel mount 21 simply by pushing wheel assembly 23 down into wheel mount 21 until it snap-locks into place.

In other embodiments (not shown), cap 15 may be made of a powdered metal and/or may be secured to housing 13 by swaging or by using one or more suitable fasteners. Also, instead of using coiled spring 25, one could use a pressurized fluid introduced at a suitable location in housing 13 to force piston 17 downwardly to its lowered position. If proceeding in such a fashion, it would be desirable to also suitably position a second seal to prevent the unwanted escape of such a pressurized fluid.

As can be appreciated, one or more pop-up wheel devices 11 may be incorporated into a work station or other material handling equipment and may be used in conjunction with other types of pop-up devices, such as pop-up balls and pop-up stops, and/or with conventional rollers or wheels. Such pop-up wheel devices 11 may be operated independently of one another and independently of other pop-up devices, rollers, or wheels. One advantage of using pop-up wheel device 11, as opposed to a pop-up ball, is that pop-up wheel device 11 has more contact area than does a pop-up ball. As a result, pop-up wheel device 11 may be better able than a pop-up ball to steer an article in a desired direction. Another advantage of using pop-up wheel device 11, as opposed to a pop-up ball, is that the contact wheel 111 of pop-up wheel device 11 can be removed from its housing (and replaced) without removing cap 15 from housing 13 whereas the primary ball of a pop-up ball cannot be removed from its housing without removing the cap from the housing.

The embodiments of the present invention described above are intended to be merely exemplary and those skilled in the art shall be able to make numerous variations and modifications to it without departing from the spirit of the present invention. All such variations and modifications are intended to be within the scope of the present invention.

What is claimed is:

1. A pop-up wheel device for use in material handling equipment, the pop-up wheel device comprising:
    (a) a housing, the housing comprising a bottom wall, a side wall extending upwardly from said bottom wall, a flange extending outwardly from the top of the side wall, and an open top;
    (b) a cap, the cap being positioned on top of the housing and being secured to the flange of the housing, the cap comprising an opening;
    (c) a piston, the piston being slidable within the housing between a lower position and an upper position;
    (d) a contact wheel, the contact wheel being freely rotatable in one direction and being coupled to the piston so that, when the piston is in the lower position, none of the contact wheel extends above the cap, and so that, when the piston is in the upper position, a portion of the contact wheel extends above the cap, wherein the contact wheel is removable from the housing and/or insertable into the housing without removing the cap from the housing; and
    (e) a nipple, the nipple being mounted in the housing for use in transmitting fluid under pressure to and from said housing for use in sliding the piston between the lower position and the upper position.

2. The pop-up wheel device as claimed in claim 1 further comprising an axle, the contact wheel being rotatably mounted on the axle.

3. The pop-up wheel device as claimed in claim 1 further comprising means for biasing the piston towards the lower position.

4. The pop-up wheel device as claimed in claim 3 wherein said biasing means comprises a coiled spring.

5. The pop-up wheel device as claimed in claim 1 further comprising a wheel mount, the contact wheel being rotatably mounted on the wheel mount, the wheel mount being coupled to the piston.

6. A pop-up wheel device for use in material handling equipment, the pop-up wheel device comprising:
    (A) a housing, the housing comprising a bottom wall, a side wall extending upwardly from said bottom wall, a flange extending outwardly from the top of the side wall, and an open top;
    (b) a cap, the cap being positioned on top of the housing and being secured to the flange of the housing, the cap comprising an opening;
    (c) a piston, the piston being slidable within the housing between a lower position and an upper position;
    (d) a contact wheel, the contact wheel being freely rotatable in one direction and being coupled to the piston so that, when the piston is in the lower position, none of the contact wheel extends above the cap, and so that, when the piston is in the upper position, a portion of the contact wheel extends above the cap;
    (e) a nipple, the nipple being mounted in the housing for use in transmitting fluid under pressure to and from said housing for use in sliding the piston between the lower position and the upper position; and
    (f) a seal, the seal being fitted around the piston and engaging the side wall of the housing to create an air-tight chamber between the piston and the housing, wherein the seal has a split, the split facing downwardly, with a first leg of the seal engaging the piston and a second leg of the seal engaging the side wall of the housing.

7. The pop-up wheel device as claimed in claim 6 wherein the housing is made of zinc-coated galvanized steel.

8. A pop-up wheel device for use in material handling equipment, the pop-up wheel device comprising:
   (a) a housing, the housing comprising a bottom wall, a side wall extending upwardly from said bottom wall, a flange extending outwardly from the top of the side wall, and an open top;
   (b) a cap, the cap being positioned on top of the housing and being secured to the flange of the housing, the cap comprising an opening;
   (c) a piston, the piston being slidable within the housing between a lower position and an upper position, the piston comprising a bottom wall, a lower side wall extending upwardly from the bottom wall, a shelf extending outwardly from a top of the lower side wall, and an upper side wall extending upwardly from an outer periphery of the shelf;
   (d) a seal, the seal being fitted around the lower side wall of the piston and engaging the side wall of the housing to create an air-tight chamber between the piston and the housing;
   (e) a nipple, the nipple being mounted in the housing for use in transmitting fluid under pressure to and from said housing for use in sliding the piston between the lower position and the upper position;
   (f) a spring for biasing the piston towards the lower position;
   (g) a wheel mount, the wheel mount comprising a first member and a second member, the first member being seated on the bottom wall of the piston and comprising a bottom, a side, a top, and a cavity extending downwardly from the top, the second member being inserted over a portion of the first member and comprising a top wall, a side wall extending downwardly from the top wall, a peripheral flange extending outwardly from a bottom of the side wall, and an open bottom, the peripheral flange of the second member being seated on the shelf of the piston; and
   (h) a wheel assembly, the wheel assembly comprising an axle and a contact wheel, the axle being disposed within the cavity of the first member of the wheel mount, the contact wheel being freely rotatable in one direction on the axle, a portion of the contact wheel extending above the wheel mount, wherein, when the piston is in the lower position, none of the contact wheel extends above the cap, and wherein, when the piston is in the upper position, a portion of the contact wheel extends above the cap.

9. The pop-up wheel device as claimed in claim 8 wherein the wheel assembly is removable from the housing and/or insertable into the housing without removing the cap from the housing.

10. A pop-up wheel device for use in material handling equipment, the pop-up wheel device comprising:
    (a) a housing, the housing comprising a bottom wall, a side wall extending upwardly from said bottom wall, a flange extending outwardly from the top of the side wall, and an open top;
    (b) a cap, the cap being positioned on top of the housing and being secured to the flange of the housing, the cap comprising an opening;
    (c) a piston, the piston being slidable within the housing between a lower position and an upper position;
    (d) a nipple, the nipple being mounted in the housing for use in transmitting fluid under pressure to and from said housing for use in sliding the piston between the lower position and the upper position;
    (e) a spring for biasing the piston towards the lower position;
    (f) a wheel mount, the wheel mount being seated on the piston; and
    (g) a wheel assembly, the wheel assembly being coupled to the wheel mount and comprising a contact wheel, the contact wheel being freely rotatable in one direction, wherein, when the piston is in the lower position, none of the contact wheel extends above the cap, wherein, when the piston is in the upper position, a portion of the contact wheel extends above the cap, and wherein the wheel assembly is removable from the housing and/or insertable into the housing without removing the cap from the housing.

11. The pop-up wheel device as claimed in claim 10 wherein the housing has a non-circular transverse cross-section.

12. The pop-up wheel device as claimed in claim 10 wherein the wheel assembly further comprises an axle, the contact wheel being rotatably mounted on the axle.

13. The pop-up wheel device as claimed in claim 10 further comprising a seal, the seal being fitted around the piston and engaging the side wall of the housing to create an air-tight chamber between the piston and the housing.

14. The pop-up wheel device as claimed in claim 13 wherein the housing is made of zinc-coated galvanized steel.

15. A pop-up wheel device for use in material handling equipment, the pop-up wheel device comprising:
    (a) a housing, the housing comprising a bottom wall, a side wall extending upwardly from said bottom wall, a flange extending outwardly from the top of the side wall, and an open top;
    (b) a cap, the cap being positioned on top of the housing and being secured to the flange of the housing, the cap comprising an opening;
    (c) a piston, the piston being slidable within the housing between a lower position and an upper position, wherein the piston comprises a bottom wall, a lower side wall extending from the bottom wall, a shelf extending from the lower side wall, an upper side wall extending from the shelf, and an open top, wherein, when viewed from above, the upper side wall is longer and wider than the lower side wall, with the shelf extending generally horizontally between the top of the lower side wall and the bottom of the upper side wall, and wherein the bottom wall slopes upwardly and then curves slightly downwardly as one moves inwardly from a periphery of the bottom wall, thereby defining a track-shaped recess spaced inwardly from the periphery of the bottom wall;
    (d) a nipple, the nipple being mounted in the housing for use in transmitting fluid under pressure to and from said housing for use in sliding the piston between the lower position and the upper position;
    (e) a spring for biasing the piston towards the lower position;
    (f) a wheel mount, the wheel mount being seated on the piston; and
    (g) a wheel assembly, the wheel assembly being coupled to the wheel mount and comprising a contact wheel, the contact wheel being freely rotatable in one direction, wherein, when the piston is in the lower position, none of the contact wheel extends above the cap, and wherein, when the piston is in the upper position, a portion of the contact wheel extends above the cap.

16. The pop-up wheel device as claimed in claim 15 wherein the wheel mount comprises a first member, the first member being seated on the bottom wall of the piston and comprising a bottom, a side, a top, and a cavity extending downwardly from the top, the first member being shaped to include at least one resilient protrusion extending into the cavity for removably snap-locking in place the wheel assembly.

17. The pop-up wheel device as claimed in claim 16 wherein the wheel mount further comprises a second member, the second member being inserted over a portion of the first member and comprising a top wall, a side wall extending downwardly from the top wall, a peripheral flange extending outwardly from a bottom of the side wall, and an open bottom, the peripheral flange of the second member being seated on the shelf of the piston.

* * * * *